United States Patent [19]

Hayafuji et al.

[11] Patent Number: 5,972,057
[45] Date of Patent: Oct. 26, 1999

[54] METHOD AND APPARATUS FOR PRODUCING DIESEL FUEL OIL FROM WASTE EDIBLE OIL

[75] Inventors: Shigeto Hayafuji; Takeo Shimidzu; Shosei Oh; Hiroaki Zaima, all of Kyoto, Japan

[73] Assignee: Lonford Development Limited, Kyoto, Japan

[21] Appl. No.: 09/146,169

[22] Filed: Sep. 3, 1998

[30] Foreign Application Priority Data

Nov. 11, 1997 [JP] Japan .................................. 9-327018
Nov. 11, 1997 [JP] Japan .................................. 9-327019

[51] Int. Cl.⁶ .................................................. C10L 1/02
[52] U.S. Cl. ............................................. 44/388; 44/386
[58] Field of Search ........................................ 44/388, 386

[56] References Cited

U.S. PATENT DOCUMENTS

| | | | |
|---|---|---|---|
| 4,364,743 | 12/1982 | Erner ........................................ | 44/388 |
| 4,695,411 | 9/1987 | Stern et al. .............................. | 44/388 |
| 5,424,466 | 6/1995 | Stern et al. ............................. | 554/175 |
| 5,424,467 | 6/1995 | Bam et al. ............................... | 554/216 |
| 5,525,126 | 6/1996 | Basu et al. ............................... | 44/388 |

FOREIGN PATENT DOCUMENTS 2560210  8/1985  France .
7-197047  8/1995  Japan .
7-310090  11/1995  Japan .

*Primary Examiner*—Jerry D. Johnson
*Attorney, Agent, or Firm*—Oblon, Spivak, McClelland, Maier & Neustadt, P.C.

[57] ABSTRACT

A production method of diesel fuel oil from waste oil, in which a vegetable diesel fuel oil can be obtained by utilizing as a raw material a waste edible oil dumped from restaurant, food industry, home, etc. and scarcely utilized. The production method comprises the steps of: removing solid materials contained in a waste edible oil; heating the waste edible oil from which solid materials have been removed to a predetermined temperature, thereby removing moisture and materials of odor contained in the waste edible oil by evaporation; dissolving in alcohol a catalyst composed of alkaline material, thereby preparing an alcoholic solution containing the catalyst; mixing the waste edible oil with the alcoholic solution containing the catalyst and stirring the waste edible oil and alcoholic solution, thereby obtaining a reaction product; separating said reaction product into a light solution and a heavy solution; mixing the light solution with a solid absorbent, thereby impurities contained in the light solution being absorbed by the solid absorbent; separating and removing the solid absorbent from a mixture of the solid absorbent having absorbed the impurities and the light solution; and mixing the heavy solution with a neutralizer to neutralize the catalyst composed of alkaline material contained in the heavy solution.

13 Claims, 5 Drawing Sheets

METHOD AND APPARATUS FOR PRODUCING DIESEL FUEL OIL FROM WASTE EDIBLE OIL

BACKGROUND OF THE INVENTION

1. Field of the Invention

The present invention relates to a method for producing a diesel fuel oil from waste edible oils in which a so-called vegetable diesel fuel oil, of which cetane index is 45 to 70, flash point is 80° C. to 210° C. and kinematic viscosity at 30° C. is 2.0 mm$^2$/s to 10.0 mm$^2$/s, is obtained from waste edible oils such as rape seed oil, sesame oil, soybean oil, maize oil, sunflower oil, palm oil, palm kernel oil, coconut oil, corn oil, safflower oil. The invention also relates to an apparatus for producing a diesel fuel oil from waste edible oils employed for carrying out the producing method.

2. Prior Arts

At present, in case of Japan, edible oils such as soybean oil mounting to about 700,000 tons, coconut oil mounting to 80,000 tons, cotton seed oil mounting to 50,000 tons, rape seed oil mounting to 700,000 tons, are used every year, and 90% of those edible oils are dumped as refuse without collection. A part of the dumped waste edible oil is carried to a refuse disposal plant in the form of mixture with other wastes and incinerated together with combustible refuse, and other part of the dumped waste edible oil is buried together with incombustible refuse. In the meantime, the remaining 10% of the waste edible oil is recycled to be employed as a raw material of soap or the like. As for the method for recycling the waste edible oil, several soap production technologies have been established including batch system comprising salting out method, continuous system comprising continuous boiling method, continuous saponification method, etc., and these soap production technologies basically comprises the steps of saponification, salting out, cleaning, and finishing boil.

It has been heretofore known that a fatty acid alkyl ester is obtained by transesterification of monoglyceride, diglyceride and triglyceride with alkyl alcohol (Organic Chemistry Handbook, issued by Gihodo, 1988, page 1407 to 1409). As for a technology for producing a diesel fuel oil from vegetable oil or waste edible oil, several attempts have been proposed. For example, the Japanese Laid-Open Patent Publication (unexamined) Hei 7-197047 discloses a method in which, with respect to 100 parts of waste edible oil, after obtaining a reaction product by heating 15 parts to 25 parts of methyl alcohol and 1 part to 2 parts of caustic soda to a reaction temperature of 45° C. to 65° C., the steps of separation by stationary layer separation, cleaning by warm water, and dehydration and drying by drying agent are carried out, whereby a diesel oil is finally obtained.

Further, the Japanese Laid-Open Patent Publication (unexamined) Hei 7-310090 discloses a production method comprising: a first step of adding alkali to a raw material of fats and oils, in such a manner as adding 15% or more by weight of methyl alcohol to 100% by weight of fats and oils and adding 0.2% by weight to 1.5% by weight of alkali to 100% by weight of fats and oils, and stirring them at a temperature of 50° C. to 64° C.; a second step of removing a precipitation of a product obtained in the first step by stationary layer separation or by centrifugation; a third step of removing methanol by heating and evaporating a supernatant obtained in the second step to a temperature higher than a boiling point of methyl alcohol; a fourth step of separating and removing a water phase from two separated phases, after adding water and acid to a product obtained in the third step for neutralization while heating to 70° C. to 90° C. thereby separating into a water phase and an oil phase; a fifth step of separating and removing a water phase, after adding water to the oil phase for washing while heating to 70° C. to 90° C.; and a sixth step of obtaining a purified fatty acid methyl ester by filtration after adding and stirring a clay to the oil phase obtained in the fifth step while heating to 100° C. to 140° C.

It is, however, unreasonable from the viewpoint of resource saving that most of the waste edible oil is dumped without being utilized, with the exception that a small percentage of waste edible oil is recycled as a raw material of soap. Moreover, when the waste edible oil is incinerated together with combustible refuse, a large amount of suspended particulate matters such as SOx, NOx, $CO_2$, CO turning to air pollutants are produced, and it is reported that deadly poisonous dioxin may be produced. On the other hand, when the waste edible oil is buried together with incombustible refuse, a soil pollution is brought about. A part of the waste edible oil dumped from restaurant, food plant, home, etc. is actually discharged into the river or lake through, which is one of the major causes of water pollution.

Recent years, under the background of increasing social concern to global environmental problems, new concept and varieties of political means on the protection of environment have been proposed. In the International Environment and Development Convention held on November, 1993, a declaration was adopted to establish a policy of getting rid of mass consumption society, in the context of reducing the environmental load due to social and economical activities as much as possible, and constructing a continuously developing society. To cope with this, on December, 1994, the Japanese government made a cabinet decision on a master plan of environmental administration, and following goals were established as specific activity program for the protection of environment to be achieved within five years: (1) reduction of waste amount by 25%. (2) reduction of combustible refuse amount occupying in the waste amount by 30%. (3) reduction of fuel amount used in energy supply facilities, etc. by 10%. etc. To achieve the foregoing goal values, recycling of plastics, container refuse, package refuse, etc. and life cycle assessment have been introduced and, at the same time, varieties of researches and developments are going on. For example, technologies including liquefaction of plastics, immobilization of $CO_2$, recycling of lubricating oil for automobile, degassing of NOx from exhaust gas have been already developed. However, the fact is that most of the waste edible oil is discharged to the environment of earth without being utilized, with the exception that a small percentage of waste edible oil is recycled as a raw material of soap.

It is certain that several attempts for producing diesel fuel oil from waste edible oil have been heretofore proposed as disclosed in the mentioned Japanese Laid-Open Patent Publications Hei 7-197047 and Hei 7-310090, but following problems exist in those known production methods:

(1) Because the waste edible oil to be utilized as a raw material is not pretreated, activity of alkali serving as a catalyst for ester exchange reaction is reduced by moisture, free fatty acid, etc., whereby conversion rate of the waste edible oil is lowered. Because a large amount of water is left in fatty acid methyl ester to be a target product, and because the waste edible oil obtained after being subject to a high temperature heating hysteresis contains a odor material produced by thermal decomposition and oxidation of vegetable oil and the odor material remains in the target product, the target product is inferior in quality. Further, because the waste edible oil contains a large amount of foreign substances or impurities such as dust, lard, solid component, not only the target product is inferior in quality but also pipe lines and valves of the production system may be clogged by those foreign substances. Furthermore, when any moisture exists in the waste edible oil, in the following reaction formula (where: R, R1, R2 and R3 indicate alkyl group, and M indicates metal), a side reaction of producing a fatty acid soap (reaction of saponification) is easy to take place, and a part of the produced fatty acid soap remains in the fatty acid methyl ester to be the target product, which brings about a turbidity. Such a fatty acid soap is difficult to separate and, after all, the product is inferior in quality.

(2) In any production method, sodium hydroxide is employed as a catalyst. However, it is to be noted that activity of sodium hydroxide with respect to the ester exchange reaction is not sufficient, and in order to improve the conversion rate of the waste edible oil to 90%, it is necessary to add methyl alcohol (stoichiometrically required amount of methyl alcohol is about 3 mole with respect to 1 mole of vegetable oil) and catalyst excessively. As the excessively added alcohol and catalyst should be removed from the target product in the subsequent process, the production process becomes complicated. Moreover, the alcohol and catalyst removed from the target product cannot be recycled, which results in increase in cost. When utilizing sodium hydroxide as a catalyst, a side reaction of producing a fatty acid soap (reaction of saponification) is easy to take place as shown in the foregoing chemical formula. And a part of the produced fatty acid soap remains in the target product, which brings about a turbidity. Such a fatty acid soap is difficult to separate and, after all, the product is inferior in quality.

(3) In the prior arts, to refine fatty acid methyl ester produced by reaction of the waste edible oil with methyl alcohol, sodium hydroxide remaining in the fatty acid methyl ester is removed through cleaning by warm water or neutralization by acid. Hence not only the production process becomes complicated, but also the reaction of saponification is accelerated all the more under the existence of warm water and sodium hydroxide. Moreover, it is difficult to remove completely the water after cleaning.

(4) Treatment of glycerol or how to recycle glycerol which is a by-product of the ester exchange reaction between the waste edible oil and methyl alcohol is not established, and after all glycerol becomes a refuse resulting in pollution of environment.

(5) Concerning the equipment for mass production of diesel fuel oil from waste edible oil and the industrial production method thereof, any fruitful performance has not been reported yet, and any industrial production technology capable of obtaining a diesel fuel oil satisfying the current JIS standard about gas oil has not been established until today.

The conventionally established soap production technology from the waste edible oil comprises the steps of saponification, salting out, cleaning and finishing boil, and other than the production of soap, this soap production technology cannot be applied to the production of diesel fuel oil, for example. It is certain that the reaction of composing fatty acid alkyl ester from edible oil by alcolysis reaction has become possible in the laboratory basis, but any technology and equipment for industrially producing diesel fuel oil has not been developed yet.

The diesel fuel oil has been conventionally produced mainly from gas oil residue of petroleum or from a product obtained by catalytic cracking or thermal decomposition of residual oil through the treatment such as reforming, desulfurization, denitrification, when required. Accordingly, such a conventional production technology cannot be applied to the production of diesel fuel oil.

SUMMARY OF THE INVENTION

The present invention was made to solve the above-discussed problems and has an object of providing a production method of diesel fuel oil from waste oil, in which a vegetable diesel fuel oil capable of being used as it is can be obtained by utilizing as a raw material a waste edible oil dumped from restaurant, food industry, home, etc. and scarcely utilized, without reforming conventional diesel vehicles adopting any gas oil derived from petroleum, and capable of utilizing effectively the food resources and contributing much to the protection of environment of the earth.

Another object of the invention is to provide a production method of diesel fuel oil from waste oil, in which glycerol which is a by-product of ester exchange reaction between waste oil and alcohol can be recycled to be used as a fuel for boiler, heat recovery type incinerator or the like, or as a raw material for collecting and producing glycerol for industrial use through the process of decomposition and purification, thereby contributing to the protection of environment of the earth.

A further object of the invention is to provide a production apparatus of diesel fuel oil from waste oil, which is preferably used for obtaining a vegetable diesel fuel oil by utilizing waste edible oil as a raw material as mentioned.

A still further object of the invention is to provide a production apparatus of diesel fuel oil from waste oil, in which glycerol which is a by-product of ester exchange reaction between waste oil and alcohol can be recycled to be used as a fuel for boiler, heat recovery type incinerator or the like, or as a raw material for collecting and producing glycerol for industrial use through the process of decomposition and purification.

To accomplish the foregoing objects, according to this invention that is characterized by obtaining a diesel fuel oil from a waste edible oil through the steps of: removing solid materials contained in a waste edible oil dumped from restaurant, food plant, home, etc. therefrom; heating said waste edible oil from which solid materials have been removed to a predetermined temperature, thereby removing moisture and materials of odor contained in the waste edible oil therefrom by evaporation; dissolving in alcohol a catalyst containing at least one type or more types of alkaline material selected from a group comprised of at least potassium hydroxide, potassium carbonate and potassium alcoholate, thereby preparing an alcoholic solution containing the catalyst; mixing said waste edible oil from which said solid materials, moisture and materials of odor have been removed with said alcoholic solution containing the catalyst and stirring the waste edible oil and alcoholic solution, thereby accelerating a catalytic reaction between the waste edible oil and the alcohol and obtaining a reaction product between the waste edible oil and the alcohol; separating said reaction product into a light solution and a heavy solution; mixing the light solution obtained in the separation step with a solid absorbent, thereby impurities such as residual catalyst, odor material, moisture contained in the light solution being absorbed by the solid absorbent; and separating and removing said solid absorbent from a mixture of the solid absorbent having absorbed the impurities and the light solution.

In the aforementioned production method, the waste edible oil is caused to react on alcohol by means of catalyst, thus a reaction product is obtained by the ester exchange reaction between the waste edible oil and alcohol. Then, through the steps of separation and purification, the values such as cetane index, flash point, kinematic viscosity, etc. finally reach the current standard of diesel fuel oil. Thus, there is provided a vegetable diesel fuel oil of which cetane index is 45 to 70, flash point is 80° C. to 210° C. and kinematic viscosity at 30° C. is 2.0 $mm^2/s$ to 10.0 $mm^2/s$, and not only all types of diesel engine can be driven by this diesel fuel oil, but also contents of sulfide and nitride are considerably low as compared with the conventional diesel fuel oil derived from petroleum.

Further, in the production method of this invention, since the solid material, moisture and odor material are removed from the waste edible oil before the reaction between the waste edible oil and alcohol, there is no more problem that activity of alkaline material serving as a catalyst for the ester exchange reaction is reduced thereby lowering conversion rate of the waste edible oil. There is no more problem of deteriorating the quality of target product due to a large amount of water, odor material, foreign substance which might remain in the fatty acid alkyl ester to be a target product. Further, there is no more problem of clogging pipe lines and valves of the production system due to the foreign substances such as lard, solid material, etc. Furthermore, since any moisture exists in the waste edible oil at the time of ester exchange reaction, the side reaction of producing a fatty acid soap (reaction of saponification) does not take place, and therefore there is no more problem that a part of the produced fatty acid soap remains in the fatty acid alkyl ester to be the target product and a turbidity is produced due to difficulty of separating the residual fatty acid soap resulting in the target product of inferior quality.

Since any sodium hydroxide is employed as a catalyst in the production method according to the invention, activity of the catalyst with respect to the ester exchange reaction is quite sufficient, and it is no more necessary to add excessively alcohol and catalyst to increase the conversion rate of the waste edible oil to 90% or more. Accordingly, any complicated process of removing the excessively added alcohol and catalyst from the product is not required, which results in an economical production cost. Since any sodium hydroxide is employed as a catalyst in the production method, the side reaction of producing a fatty acid soap (reaction of saponification) does not take place, and therefore there is no more problem that a part of the produced fatty acid soap remains in the fatty acid alkyl ester to be the target product and a turbidity is produced resulting in the target product of inferior quality.

In the production method of this invention, the alcohol solution containing a catalyst and the waste edible oil are mixed to react on each other after preliminarily dissolving the alcohol in the catalyst, and as a result of employing such a step, reaction speed is considerably improved as compared with the process of adding a catalyst directly to the mixed solution of waste edible oil and alcohol and stirring them for the reaction between the waste edible oil and alcohol.

In the production method of this invention, to purify the fatty acid alkyl ester produced by the reaction between the waste oil and alcohol, the impurities such as residual catalyst, odor material, coloring material, moisture contained in the light solution is absorbed by the solid absorbent, and the solid absorbent having absorbed the impurities are separated and removed from the light solution. This purification process is simple as compared with the process of removing the residual catalyst remaining in the fatty acid alkyl ester through cleaning by warm water or by neutralization by acid, and there is no more possibility of accelerating the reaction of saponification, and it is no more necessary to remove water after the cleaning.

The invention is further directed to a production apparatus for producing a diesel fuel oil from a waste edible oil. The production apparatus comprises: a waste edible oil storage tank for storing a waste edible oil dumped from restaurant, food plant, home, etc.; solid material removing means for removing solid materials contained in said waste edible oil therefrom; waste edible oil heating means for heating said waste edible oil from which solid materials have been removed to a predetermined temperature; dehydrating and deodorizing means for removing moisture and odor material contained in said heated waste edible oil by evaporation therefrom; a dissolving and stirring tank for mixing a catalyst composed of an alkaline material with alcohol and stirring the catalyst and alkaline material, thereby preparing a catalyst containing alcohol solution in which the catalyst is dissolved; alcohol supplying means for supplying an alcohol to said dissolving and stirring tank; catalyst supplying means for supplying the catalyst to said dissolving and stirring tank; a stirring and reaction tank for mixing said waste edible oil from which solid materials moisture and odor material have been removed with said alcohol solution containing the catalyst, and accelerating a catalytic reaction between the waste edible oil and alcohol, thereby obtaining a reaction product between the waste edible oil and alcohol; liquid-liquid separating means for separating said reaction product into a light solution and a heavy solution; a stirring and purifying tank for mixing and stirring said light solution obtained by separation from said reaction product with a solid absorbent so that impurities contained in the light solution such as residual oxygen, odor material, coloring material, moisture, etc. are absorbed by the solid absorbent; absorbent supplying means for supplying the solid absorbent to said stirring and purifying tank; and solid-liquid separating means for separating and removing the solid absorbent from a mixture of said solid absorbent having absorbed the impurities and said light solution.

In the production apparatus as defined in the above, the waste edible oil dumped from restaurant, food plant, home, etc. is stored in the waste edible oil storage tank, and first solid materials are removed from the waste edible oil by the solid material removing means. After being heated to a predetermined temperature by the waste edible oil heating means, moisture and odor material are removed by evaporation from the waste edible oil from which solid materials have been removed by the dehydrating and deodorizing means. Then, an alcohol is supplied to the dissolving and stirring tank by the alcohol supplying means, and a catalyst composed of an alkaline material is supplied to the dissolving and stirring tank by the catalyst supplying means, thus the catalyst is mixed into the alcohol in the dissolving and stirring tank, whereby a catalyst containing alcohol solution in which catalyst is dissolved in the alcohol is prepared. Further, by mixing and stirring the waste edible oil from which solid material, moisture and odor material have been removed with the mentioned catalyst containing alcohol solution, the waste edible oil is caused to react on the alcohol by the catalyst, whereby a reaction product is obtained as a result of an ester exchange reaction between the waste edible oil and the alcohol. The reaction product thus obtained is then separated into a light solution and a heavy solution by the liquid-liquid separating means. The light solution obtained by the separation from the reaction product is introduced into the stirring and purifying tank, and a solid absorbent is supplied to the stirring and purifying tank by the absorbent supplying means. Thus, in the stirring and purifying tank, by mixing and stirring the light solution with the solid absorbent, the impurities contained in the light solution such as residual oxygen, odor material, coloring material, moisture, etc. are absorbed by the absorbent. The mixture of the absorbent having absorbed the impurities and the light solution is then separated into the solid absorbent and the light solution by the solid-liquid separating means, whereby a purified light solution principally composed of fatty acid alkyl ester is obtained.

Other objects, features and advantages of the invention will become apparent in the course of the following description with reference to the accompanying drawings.

DESCRIPTION OF THE PREFERRED EMBODIMENTS

Several examples of the invention are hereinafter described with reference to FIGS. 1 to 5.

Figure 1:
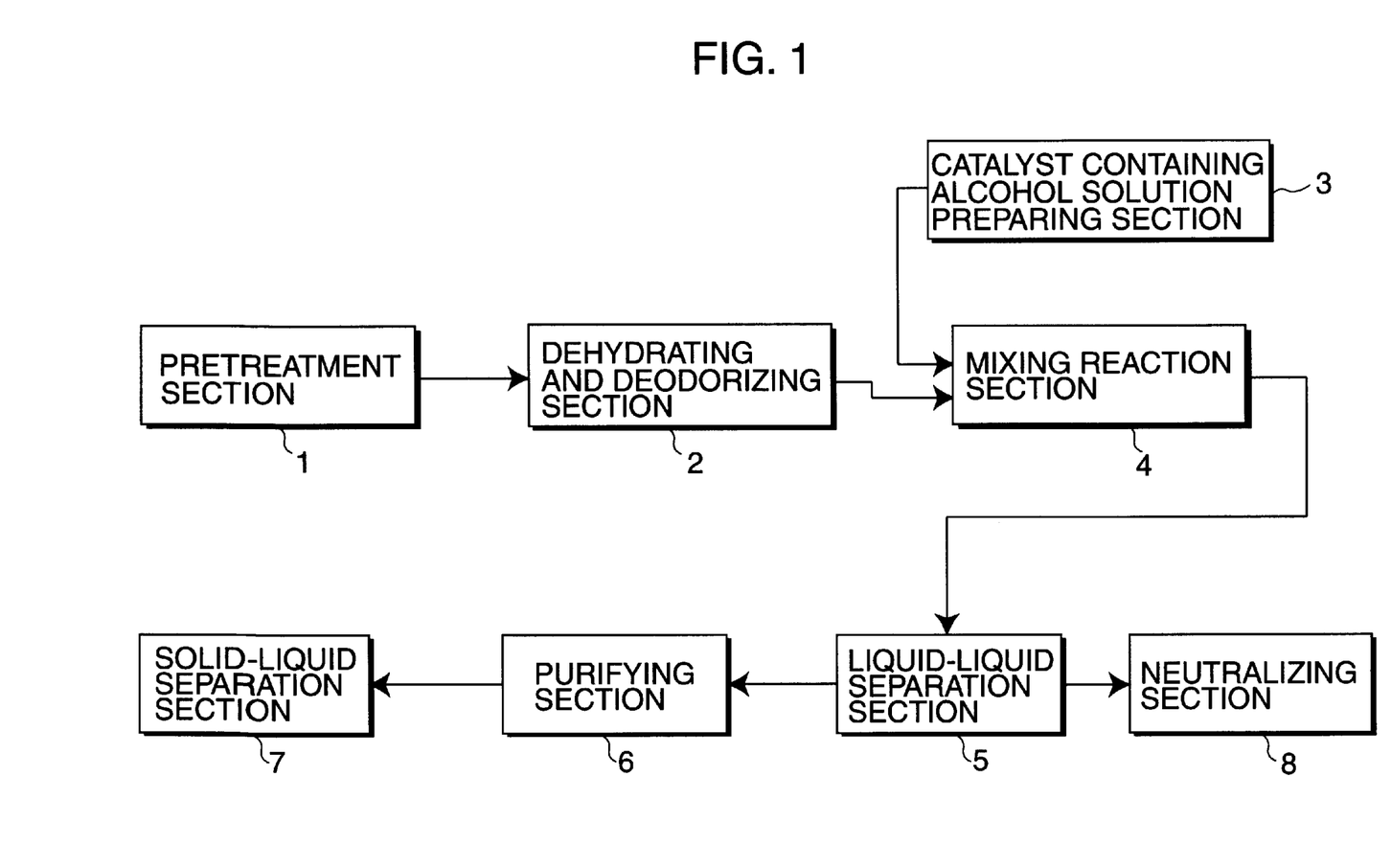
FIG. 1 is a schematic block diagram showing an example of the entire arrangement of the apparatus used for carrying out the production method of a diesel fuel oil from a waste edible oil in accordance with the present invention.
Figure 3:
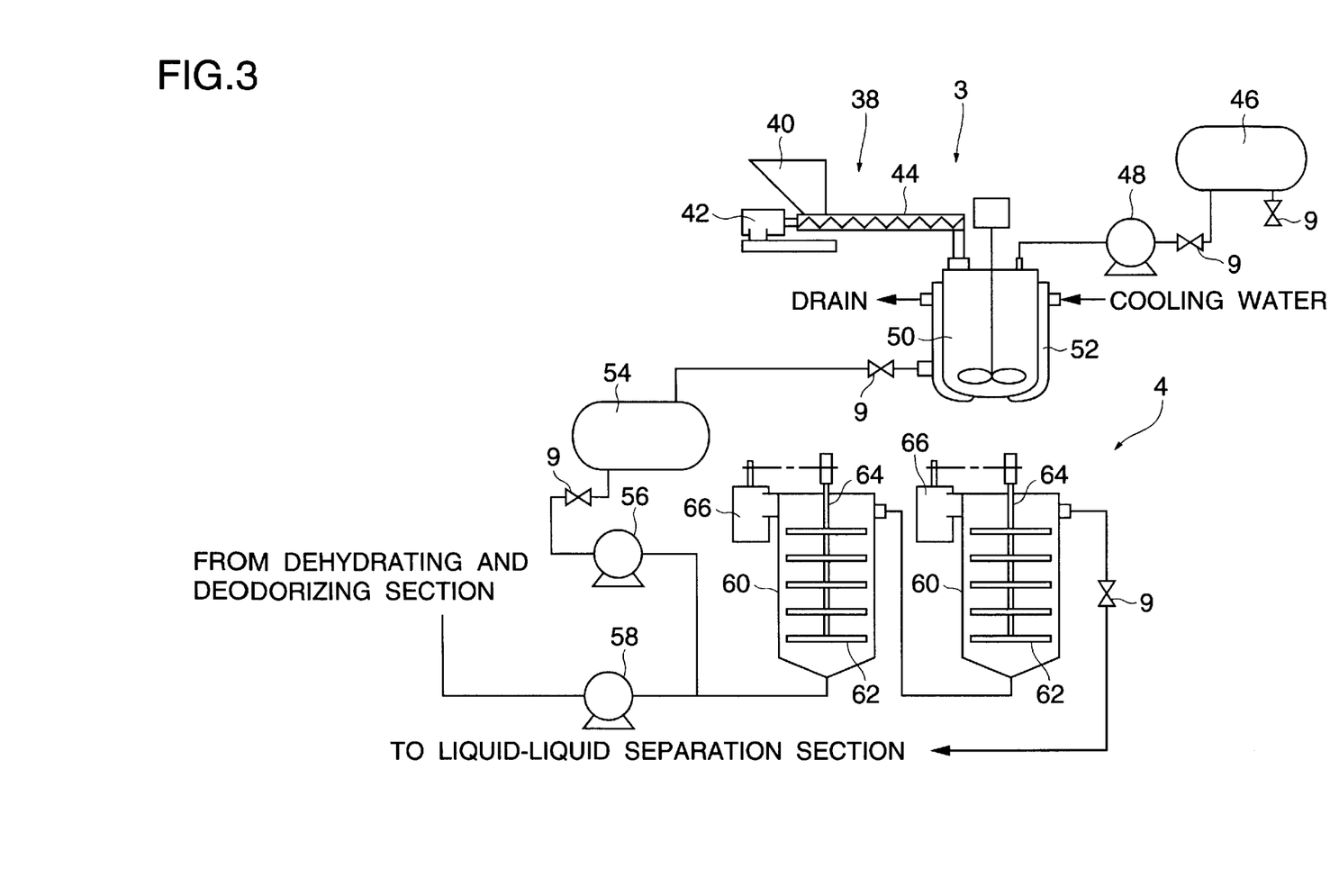
FIG. 3 is a schematic diagram showing the arrangement of the catalyst containing alcohol solution preparing section and the mixing reaction section of the same apparatus.
Figure 4:
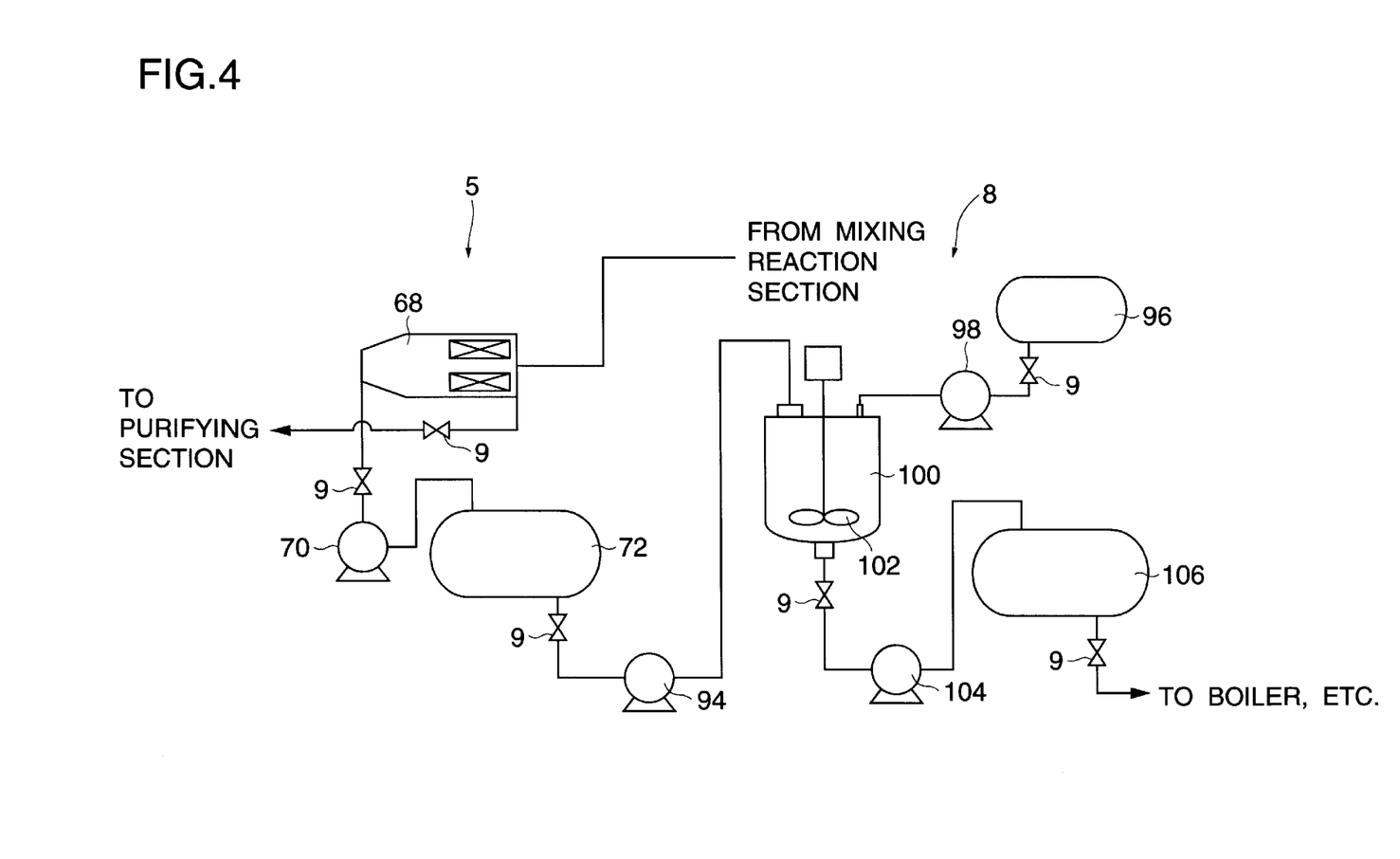
FIG. 4 is a schematic diagram showing the arrangement of the liquid-liquid separation section and the neutralizing section of the same apparatus.
Figure 5:
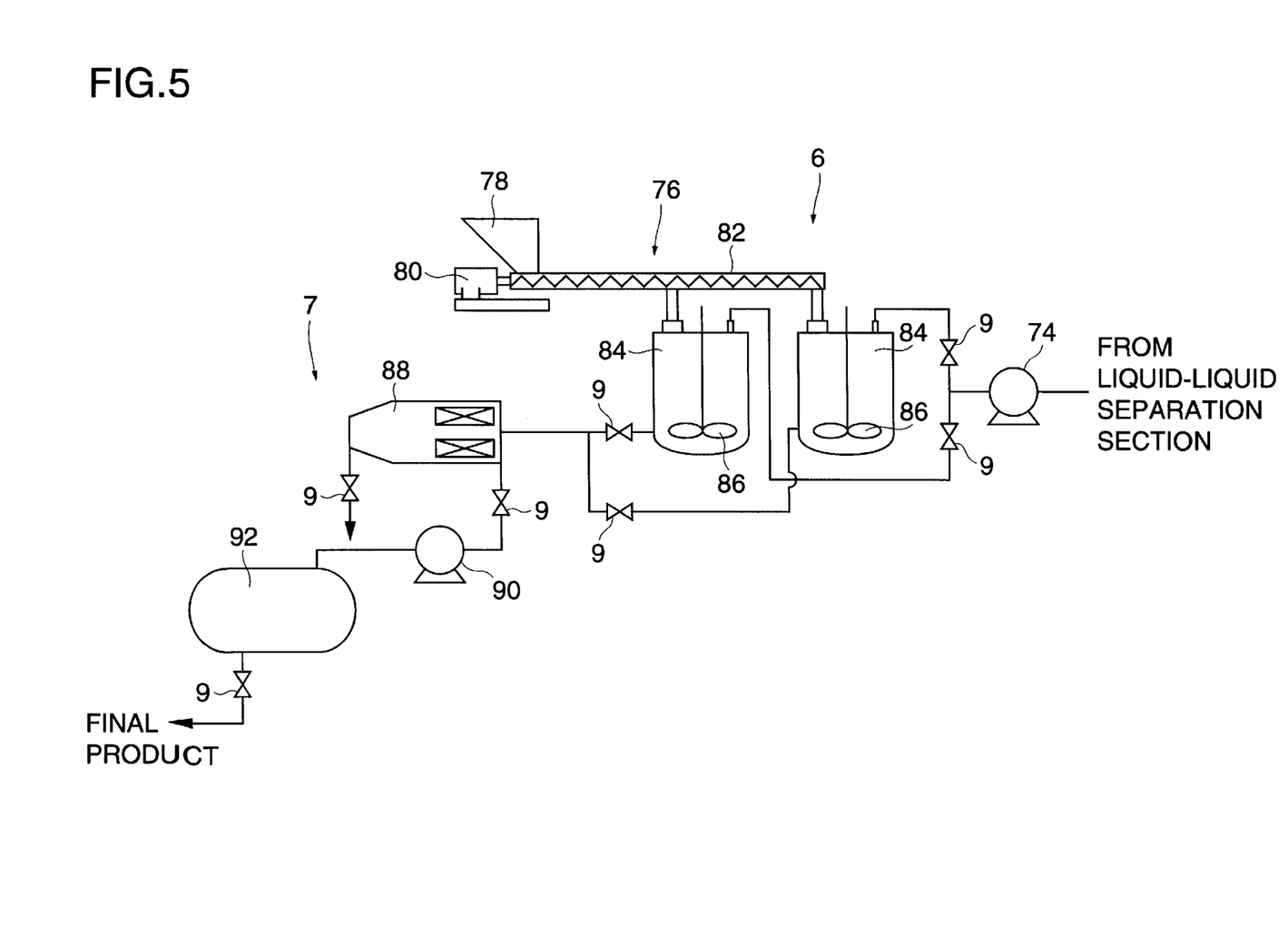
FIG. 5 is a schematic diagram showing the arrangement of the purifying section and the solid-liquid separation section of the same apparatus.

First, an example of an arrangement of the apparatus for carrying out the production method of a diesel fuel oil from a waste edible oil according to the invention is hereinafter described with reference to FIGS. 1 to 5. As shown in FIG. 1 the production apparatus of diesel oil comprises a pretreatment section 1 a dehydrating and deodorizing section 2, a catalyst containing alcohol solution preparing section 3, a mixing reaction section 4, a liquid-liquid separation section 5, a purifying section 6, a solid-liquid separation section 7, and a neutralizing section 8. In addition, an arrangement of the pretreatment section 1 and that of the dehydrating and deodorizing section 2 are shown in FIG. 2, an arrangement of the catalyst containing alcohol solution preparing section 3 and that of the mixing reaction section 4 are shown in FIG. 3, an arrangement of the liquid-liquid separation section 5 and that of the neutralizing section 8 are shown in FIG. 4, and an arrangement of the purifying section 6 and that of the solid-liquid separation section 7 are shown in FIG. 5, respectively.

Figure 2:
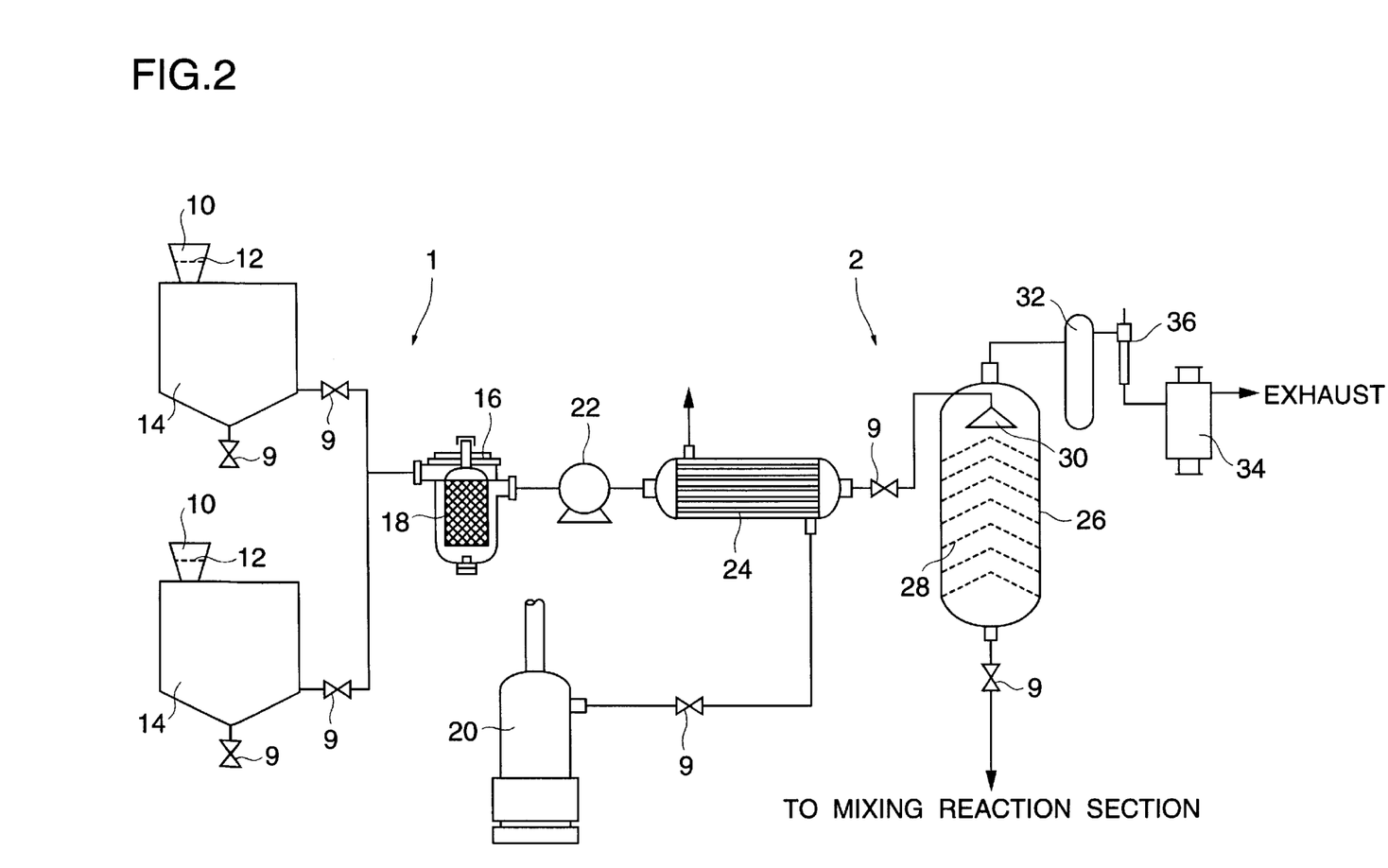
FIG. 2 is a schematic diagram showing the arrangement of the pretreatment section and the dehydrating and deodorizing section each forming a part of the production apparatus of the diesel fuel oil shown in FIG. 2.

As shown in FIG. 2, the pretreatment section 1 comprises a waste edible oil introduction chute 10, waste edible oil storage tanks 14, and a strainer 16 mounted with a cartridge type filter 18. A waste edible oil is introduced from the waste edible oil introduction chute 10, and by passing through a filter 12 composed of a stainless steel gauge of 10 to 100 in mesh number, solid materials contained in the waste edible oil are primarily removed, and then by passing through the strainer 16, the solid materials contained in the waste edible oil are further removed.

Two waste edible oil storage tanks 14 are installed, and while one waste edible oil storage tank 14 is supplying the waste edible oil, the other waste edible oil storage tank 14 is on stand by. As the waste edible oil stored in the waste edible oil storage tank 14 is kept to be stationary in the stand-by state, a part of the solid materials, excessive moisture, etc. contained in the waste edible oil is naturally precipitated due to difference in specific gravity, and those naturally precipitated solid materials, excessive moisture, etc. are discharged with a certain interval through a drain discharge port provided at the bottom of the waste edible oil storage tank 14. Further, the waste edible oil from which the solid materials and moisture have been primarily removed is then caused to pass through the strainer 16 mounted with the cartridge type filter 18 of 10 to 100 in mesh number, whereby fine solid materials contained in the waste edible oil have are secondarily removed, and a waste edible oil of which content of solid materials is 0.05% or less, for example, is obtained. In the drawings, reference numeral 9 designates valves.

The dehydrating and deodorizing section 2 comprises a boiler 20 for generating a steam, a pump 22 for measuring waste edible oil, a shell and heat exchanger 24, a vacuum dehydrating and deodorizing tower 26 mounted with a plurality of conical perforated plates 28 and with a dispersion nozzle 30, and an evacuator 34 mounted with a vacuum gauge 36. The waste edible oil from which solid materials have been removed in the pretreatment section 1 is heated to a temperature required in the subsequent vacuum dehydration and deodorization process by the heat exchange with steam during passing through the shell and heat exchanger 24, then is introduced to the vacuum dehydrating and deodorizing tower 26 through the dispersion nozzle 30. The waste edible oil introduced in the vacuum dehydrating and deodorizing tower 26 is dehydrated and deodorized during flowing downstream through the plurality of conical perforated plates 28 in order. In other words, the moisture and odor material of low melting point contained in the waste edible oil heated to a predetermined temperature are evaporated (vaporized) speedily under the vacuum of 1 to 100 mmHg and discharged from the upper exit of the vacuum dehydrating and deodorizing tower 26, then are cooled in the condenser 32 to be transformed again into a liquid and discharged outside. In this manner, the waste edible oil is dehydrated and deodorized to be, for example, 0.03% in content of moisture and 10 ppm in content of odor material.

As shown in FIG. 3, the catalyst containing alcohol solution preparing section 3 comprises a catalyst feeder 38 comprised of a catalyst introduction chute 40, a drive motor 42 and a screw conveyor 44; an alcohol storage tank 46; an alcohol measuring pump 48; a dissolving and stirring tank 50 provided with a cooling water jacket 52; and a catalyst containing alcohol solution tank 54. Preparation of the catalyst containing alcohol solution is carried out by batch system, and in which first an alcohol is sent from the alcohol storage tank 46 into the dissolving and stirring tank 50 by the measuring pump 48, then a catalyst supplied from the catalyst feeder 38 is supplied into the dissolving and stirring tank 50 at a predetermined ratio of catalyst to the alcohol while stirring the alcohol introduced in the dissolving and stirring tank 50, and stirring is carried out until the catalyst has completely dissolved in the alcohol. The heat of dissolution generated at the time of dissolving the catalyst in alcohol is removed by the heat exchange between a cooling water and the catalyst containing alcohol solution performed by dashing the cooling water into the internal part of the cooling water jacket 52. Supply speed of the catalyst to the dissolving and stirring tank 50 is controlled so that temperature of the catalyst containing alcohol solution does not exceed 64° C. when the alcohol is methyl alcohol. If the supply speed of the catalyst is higher, the generated heat of dissolution is not removed in time. If temperature of the solution exceeds the boiling point of alcohol, evaporation of alcohol takes place briskly and bumping due to local overheat of the solution occurs, which brings about a danger. After charging a predetermined amount of catalyst into the dissolving and stirring tank 50 and completing the dissolution of the catalyst in alcohol, a valve 9 on the side of the dissolving and stirring tank 50 is opened, whereby the solution is transferred to the catalyst containing alcohol solution tank 54. Subsequently, alcohol and catalyst are introduced in the dissolving and stirring tank 50 in the same manner as the foregoing, and like dissolving and stirring operation is repeated.

The mixing reaction section 4 comprises a measuring pump 56 for catalyst containing alcohol solution, a measuring pump 58 for dehydrated and deodorized waste edible oil, and stirring and reaction tanks 60 each provided with multistage blades 62. In each stirring and reaction tank 60, the multistage blades 62 are mounted on a rotary shaft 64 disposed in the center part of a cylindrical vessel, and by rotating the rotary shaft 64 by a drive motor 66, the dehydrated and deodorized waste edible oil moving from the bottom part to the upper part and the catalyst containing alcohol solution are continuously mixed in the stirring and reaction tank 60, whereby a reaction takes place between the waste edible oil and alcohol. Note that two stirring and reaction tanks 60 in cascade connection are installed, and in which the waste edible oil sent from the vacuum dehydrating and deodorizing tower 26 and the catalyst containing alcohol solution sent from the catalyst containing alcohol solution tank 54 are introduced in the bottom part of the first stirring and reaction tank 60 continuously at a certain rate by the measuring pumps 56, 58, and after passing through the internal part of the first stirring and reaction tank 60, they are discharged from the outlet of the first stirring and reaction tank 60. Then the waste edible oil and the catalyst containing alcohol solution are introduced in the second stirring and reaction tank 60, and after passing through the internal part of the second stirring and reaction tank 60, they are discharged from the outlet of the second stirring and reaction tank 60. Introduction speed of the waste edible oil and catalyst containing alcohol solution is controlled such that the waste edible oil and alcohol are mixed with each other and an ester exchange reaction of the waste edible oil proceeds in the respective stirring and reaction tanks 60, and that the reaction comes to an end at the outlet of the second stirring and reaction tank 60.

The liquid-liquid separation section 5 comprises a liquid-liquid centrifugal separator 68, a liquid feed pump 70, and a heavy solution storage tank 72, as shown in FIG. 4. The liquid-liquid centrifugal separator 68 is disposed at a position lower than the outlet of the stirring and reaction tank 60, whereby a reaction product flowing out of the stirring and reaction tank 60 naturally flows in the liquid-liquid centrifugal separator 68 due to the difference in height between the stirring and reaction tank 60 and the liquid-liquid centrifugal separator 68. Then, in the liquid-liquid centrifugal separator 68, the reaction product is separated into a light solution principally composed of fatty acid alkyl ester and a heavy solution principally composed of glycerol. The heavy solution is sent to a heavy solution storage tank 72 by the liquid feed pump 70 and stored therein, and the light solution is sent to the purifying section 6.

The purifying section 6 comprises a light solution measuring pump 74, an absorbent feeder 76 comprised of an absorbent supply chute 78, a drive motor 80 and a screw conveyor 82, and stirring and purifying tanks 84 each provided with a stirring blade 86, as shown in FIG. 5. Note that two stirring and purifying tanks 84 in parallel connection are installed, and operation in the respective stirring and purifying tanks 84 is carried out in batch system. A semi-continuous operation is carried out by switching a pair of valves 9 disposed on the introduction port side of the respective stirring and purifying tanks 84 and by switching a pair of charging ports disposed on the screw conveyor 82 of the absorbent feeder 76. A predetermined rate of absorbent, with respect to the light solution introduced from the liquid-liquid separation section 5 into the stirring and purifying tanks 84, is charged from the absorbent feeder 76 into the stirring and purifying tanks 84. Then, in the stirring and purifying tanks 84, the light solution is continuously stirred until the impurities in the light solution such as alkaline component, moisture, odor material, coloring material, etc. are completely absorbed. After completing the stirring, the valves on the side of the stirring and purifying tanks 84 are opened, and the contents of the stirring and purifying tanks 84 are supplied to the solid-liquid separation section 7.

The solid-liquid separation section 7 comprises a solid-liquid centrifugal separator 88, a liquid feed pump 90, and a purified liquid solution storage tank 92. The solid-liquid centrifugal separator 88 is disposed at a position lower than the discharge ports of the stirring purifying tanks 84, so that the mixture of the light solution flowing out of the stirring and purifying tanks 84 and the absorbent naturally flows in the solid-liquid centrifugal separator 88 due to the difference in height between the stirring and purifying tanks 84 and the solid-liquid centrifugal separator 88. In the solid-liquid centrifugal separator 88, the mixture is separated into a used solid absorbent and a purified light solution which is a target product. The separated or extracted light solution is sent to the purified light solution storage tank 92 by the liquid feed pump 90 to be stored therein, while the absorbent being discharged outside the system to be recovered or disposed.

The neutralizing section 8 comprises a heavy solution measuring pump 94, an acid storage tank 96, an acid measuring pump 98, a neutralizing and stirring tank 100 provided with a stirring blade 102, a liquid feed pump 104, and a neutralized heavy solution storage tank 106, as shown in FIG. 4. The neutralization of the heavy solution is carried out by an operation of batch system, and in which a predetermined amount of acid, with respect to the heavy solution introduced from the heavy solution storage tank 72 into the neutralizing and stirring tank 100 by the heavy solution measuring pump 94, is fed from the acid storage tank 96 into the neutralizing and stirring tank 100 by the acid measuring pump 98. Then, the heavy solution is sufficiently stirred in the neutralizing and stirring tank 100, and after completing the stirring, the heavy solution is fed into the heavy solution storage tank 106 to be stored therein, and is utilized as a fuel for boiler or as a raw material to produce glycerol for industrial use.

To produce a diesel fuel oil of high quality, using the production apparatus arranged as shown in FIGS. 1 to 5, from a waste edible oil dumped by the reaction of catalyst on alcohol from restaurant, food plant, home, etc., following eight steps are carried out in order.

(1) a waste edible is charged in the waste edible oil introduction chute 10 of the pretreatment section 1, solid materials contained in the waste edible oil are primarily removed by the filter 12 composed of a wire gauge mounted on the waste edible oil introduction shoot 10, and after the natural precipitation of the solid materials and before sending the supernatant to the dehydrating and deodorizing section 2, the solid materials still remaining in the waste edible oil are secondarily removed by the strainer 16 disposed on the outlet side of the waste edible oil storage tanks 14.

(2) The waste edible oil from which solid materials have been removed is sent to the heat exchanger 24 by the waste edible oil measuring pump 22 and heated to a predetermined temperature in the heat exchanger, and moisture and odor material of low boiling point are evaporated in the vacuum dehydrating and deodorizing tower 26, thus dehydration and deodorization are carried out.

(3) A predetermined amount of catalyst and alcohol are respectively introduced in the dissolving and stirring tank 50 by the catalyst feeder 38 and the alcohol measuring pump 48, and after dissolving the catalyst in the alcohol by stirring the catalyst and alcohol in the dissolving and stirring tank 50, the solution is introduced in the catalyst containing alcohol solution tank 54 to be stored therein.

(4) The dehydrated and deodorized waste edible oil and catalyst containing alcohol solution are sent at a predetermined ratio from the dehydrating and deodorizing section 2 and the catalyst containing alcohol solution tank 54 into the cascade-connected stirring and reaction tanks 60 by the measuring pumps 56, 58 respectively. Then, in the stirring and reaction tanks 60 each provided with multistage blades 62, the dehydrated and deodorized waste edible oil heated to a predetermined temperature and the catalyst containing alcohol solution are stirred and mixed to proceed a reaction between the waste edible oil and alcohol, and after obtaining a reaction product between the waste edible oil and alcohol, the reaction product is continuously transferred to the liquid-liquid centrifugal separator 68.

(5) In the liquid-liquid centrifugal separator 68, the reaction product is separated into a light solution and a heavy solution, and the light solution is sent to the purifying section 6 by the light solution measuring pump 74, and the heavy solution is introduced into the heavy solution storage tank 72.

(6) A predetermined amount of absorbent is added to the light solution introduced into the stirring and purifying tanks 84 by the absorbent feeder 76, and after absorbing impurities contained in the light solution, with strong stirring by the stirring blades 86, in the stirring and purifying tanks 84, a mixture of the absorbent having absorbed the impurities and the light solution is sent to the solid-liquid centrifugal separator 88.

(7) In the solid-liquid centrifugal separator 88, the absorbent and the purified light solution are separated from each other, and the absorbent is discharged outside the system, and the purified light solution is introduced in the purified light solution storage tank 92 to be stored therein as a target product.

(8) The heavy solution and an acid are sent at a predetermined rate from the heavy solution storage tank 72 and the acid storage tank 96 into the neutralizing and stirring tank 100 by the measuring pumps 94, 98 respectively, and in the neutralizing and stirring tank 100, the heavy solution and the acid are stirred and mixed, whereby the catalyst composed of alkaline materials and contained in the heavy solution are neutralized by the acid. The heavy solution which has been neutralized by the neutralizing reaction is then sent to the heavy solution storage tank 106 to be stored therein, and the heavy solution are utilized as a fuel for boiler or as a raw material for production of glycerol for industrial use.

By carrying out the foregoing eight steps, it becomes possible to obtain from a waste edible oil a heavy solution to be finally utilized as a vegetable diesel fuel oil, as a fuel for boiler or as a raw material to produce glycerol for industrial use.

The waste edible oils each serving as a raw material include waste rape seed oil, waste sesame oil, waste soybean oil, waste maize oil, waste sunflower oil, waste palm oil, waste palm kernel oil, waste coconut oil, waste corn oil, waste safflower oil, etc., and either one of them or a mixture of the mentioned several waste edible oils is employed as a raw material. There is no particular requirement regarding the quality of waste edible oil, but it is generally preferable that the waste edible oil has less content of moisture and solid component.

The filter 12 mounted on each waste edible oil introduction chute 10 to remove the solid materials in the pretreatment section 1 is a wire gauge of stainless steel of 10 to 100 in mesh number, and performs to remove relatively large dust or impurities contained in the waste edible oil. On the other hand, the cartridge type filter 18 of 100 to 600 in mesh number is mounted on the strainer 16 disposed on the outlet side of the waste edible oil storage tanks 14, and performs to remove relatively small size dust or impurities contained in the waste edible oil.

The waste edible oil sent from the waste edible oil storage tanks 14 to the heat exchanger 24 at a predetermined flow rate by the measuring pump 22 is heated to a temperature of 25° C. to 200° C. by heat exchange with a steam sent from the boiler 20, and adjusted to be easily and perfectly dehydrated and deodorized in the vacuum dehydrating and deodorizing tower 26. Further, considering the temperature drop of the waste edible oil due to heat of evaporation of moisture and odor material in the dehydrating and deodorizing tower 26, it is necessary to control the temperature of the waste edible oil at the outlet of the heat exchanger 24 so that the temperature of the mixed solution after mixing the dehydrated and deodorized waste edible oil and the catalyst containing alcohol solution of room temperature in the stirring and reaction tanks 60 is in the temperature range of easy reaction.

Absolute pressure in the internal part of the vacuum dehydrating and deodorizing tower 26 depends on moisture contained in the waste edible oil, content of the odor material, and temperature of the waste edible oil, and is adjusted to be in the range of 1 to 100 mmHg. If the absolute pressure in the internal part of the vacuum dehydrating and deodorizing tower 26 is excessively high, the moisture and odor material cannot be sufficiently removed. On the other hand, if the absolute pressure is excessively low, even useful and available component in the waste edible oil may be removed, and energy is wasted.

A mixture of one type or more types of alcohol selected from a group comprised of alkyl alcohol of which number of carbon is 1 to 10 such as methyl alcohol, ethyl alcohol, isobutyl alcohol is employed as an alcohol acting on the waste edible oil. Strict purity of alcohol is not particularly required, but content of moisture is desirably smaller. As for the type of alcohol, either unsaturated or saturated alkyl alcohol of which number of carbon is 1 to 10 is available, and lower alcohol such as methyl alcohol, ethyl alcohol, etc. of small number of carbon is more suitable for obtaining a vegetable diesel fuel oil of high quality.

One type or more types of alkaline material selected from a group of potassium hydroxide, potassium carbonate, and potassium alcoholate such as potassium methylate, potassium ethylate, etc. may be employed as a catalyst for reaction between the alcohol and waste edible oil. It is also preferable to use a catalyst mixed with sodium catalyst. When using those catalysts, conversion rate from the waste edible oil to fatty acid alkyl ester is improved as compared with that using sodium hydroxide as the catalyst, and not only a vegetable diesel fuel oil of high quality is obtained but also the saponification reaction shown in the mentioned chemical formula is restrained. For example, when performing an ester exchange reaction between 99.8% methyl alcohol and a waste edible oil containing 0.5% moisture using sodium hydroxide and separating a reaction product by a centrifugal separator, a fatty acid soap was detected in the obtained light solution, a turbidity was observed, and the fatty acid soap was also detected in the heavy solution. On the other hand, when performing a reaction of like waste edible oil on 99.8% methyl alcohol, a transparent light solution was obtained, and any fatty acid soap was not detected at all.

Converting into a ratio by weight of catalyst to waste edible oil, dissolving amount of catalyst in alcohol is preferably 0.3% by weight to 3.0% by weight and, more preferably, 0.6% by weight to 2.0% by weight. Concerning the additive amount of alcohol solution containing a catalyst to waste edible oil, converting into a ratio of alcohol to waste edible oil, the additive amount of alcohol to 100 g of waste edible oil is preferably 0.15 mol to 0.75 mol and, more preferably, 0.25 mol to 0.35 mol. Within a certain range of additive amount of catalyst, when additive amount of catalyst is larger, equilibrium conversion of waste edible oil defined by the expression [equilibrium conversion of waste edible oil=waste edible oil transformed into fatty acid alkyl ester/(waste edible oil as raw material−impurities)×100%] becomes higher. However, when exceeding the certain range, the equilibrium conversion of waste edible oil becomes almost constant, and the side reaction of producing fatty acid soap is easy to occur. When additive amount of catalyst is excessively large beyond the certain range, corrosiveness on the reaction apparatus becomes strong, and it becomes necessary to establish more strict conditions of purification of the reaction product, and therefore appropriate additive amount of catalyst is essential.

Within a certain range of additive amount of alcohol, when additive amount of alcohol is larger, equilibrium conversion of waste edible oil becomes higher. However, when exceeding the certain range, the equilibrium conversion of waste edible oil becomes almost constant, and excessive alcohol is left in the product after the reaction. Such an excessive alcohol is not only useless but also gives undesirable influence on the quality of target product. Generally, to transform monoglyceride, diglyceride and triglyceride which are principal components of the waste edible oil into fatty acid ester, about 3 mol of alcohol is stoitiometrically required with respect to 1 mol of waste edible oil. However, it is preferable that a larger amount than that stoichiometrically required, i.e., stoichiometric quantity or larger quantity than that by 10%, is added to obtain a diesel fuel oil of higher quality.

In the dissolution of catalyst in alcohol in the dissolving and stirring tank 50, to prevent the boiling or bumping of alcohol due to partial overheat by heat of dissolution, it is necessary to add the catalyst at a predetermined speed while stirring the alcohol, after introducing the alcohol into the dissolving and stirring tank 50. Further, to eliminate the heat of dissolution, a cooling water is applied to the jacket 52 of the dissolving and stirring tank 50, and flow rate of the cooling water is adjusted so that temperature of the catalyst containing alcohol solution is kept to a temperature not higher than the boiling point.

In the production method according to the invention, the reaction between the catalyst containing alcohol and the waste edible oil is caused to take place, after dissolving the catalyst for accelerating the reaction between the alcohol and waste edible oil in alcohol. By employing such a production method, reaction speed is remarkably improved as compared with the method of inputting the catalyst directly into the stirring and reaction tank 60. For example, when mixing the catalyst containing alcohol solution and the waste edible oil to react on each other after dissolving potassium hydroxide in methyl alcohol, a reaction time necessary for the waste edible oil to reach an equilibrium conversion of 99% is not longer than 1.0 min at a reaction temperature of 60° C. and at a stirring speed of 300 rpm. On the other hand, when methyl alcohol and catalyst are simultaneously added to the waste edible oil for the same reaction, the reaction time necessary for the waste edible oil to reach an equilibrium conversion of 96% is as long as 30 min under the same conditions. Thus, in the production method according to the invention, not only the operation of reaction between the alcohol and waste edible oil which could be carried out just by batch system can be now carried out in the form of continuous operation, but also reaction speed is considerably improved. More specifically, as shown in FIG. 3, two stirring and reaction tanks 60 each provided with multi-stage blades 62 are installed in cascade connection, and a reaction product (waste edible oil and catalyst containing alcohol solution) is introduced into the bottom part of the first stirring and reaction tank 60 and caused to pass through the internal part of the stirring and reaction tank 60. Then, the reaction product discharged out of the outlet of the first stirring and reaction tank 60 is introduced into the bottom part of the second stirring and reaction tank 60 and caused to pass through the internal part of the stirring and reaction tank 60, and discharged out of the discharge port. Note that the stirring and reaction tanks 60 are designed to have their height so that total staying time of the reaction product in the two stirring and reaction tanks 60 for the mentioned series of process is 1.0 min or less.

In the reaction between the waste edible oil and alcohol in the stirring and reaction tanks 60, temperature is in the range of room temperature (25° C.) to 240° C. pressure is in the range of atmospheric pressure to 78.5 kg/cm$^2$, preferably, to 20 kg/cm$^2$, and in this case, the equilibrium conversion of the waste edible oil reaches 10% to 99.9%. Because the reaction between the waste edible oil and alcohol is a reversible reaction, to make maximum the equilibrium conversion of the waste edible oil, optimum conditions of temperature and pressure are required. When increasing the temperature, the reaction speed is higher, and at the same time pressure in the system becomes also high and any high pressure reactor is required, which brings about a disadvantage in cost. When increasing the temperature to a boiling point of alcohol or more, the alcohol is evaporated and the reaction must take place between the gas alcohol and liquid waste edible oil, which results in a low equilibrium conversion.

As shown in the mentioned chemical formula, the reaction product flowing out of the stirring and reaction tanks 60 is a mixture principally composed of fatty acid alkyl ester and glycerol produced by the ester exchange reaction between triglyceride, which is a principal component of vegetable oil, and alcohol. To separate the fatty acid alkyl ester and glycerol from each other, a stationary layer separation utilizing a difference in specific gravity between the fatty acid alkyl ester and glycerol has been conventionally employed. In this separation method, however, it takes a long time to completely separate the fatty acid alkyl ester and glycerol from each other, resulting in low productivity. In the apparatus according to the invention, complete separation of the fatty acid alkyl ester and glycerol from each other can be efficiently carried out by centrifugal separation. As a small amount of catalyst, unreacted alcohol, odor material, coloring material, etc. are left in the light solution flowing out of the liquid-liquid centrifugal separator 68, it is necessary for the light solution to be sent to the purifying section 6 and purified there. Further, as the heavy solution contains most part of the catalyst used in the reaction in addition to the glycerol which is a principal component, if the heavy solution is used as a fuel or as a raw material for production of glycerol as it is, a corrosion due to alkali takes place in the apparatus. Therefore, the heavy solution is sent to the neutralizing section 8 where neutralization by acid is carried out. To purify the light solution of which principal component is fatty acid alkyl ester, one type of absorbent or a mixture of two or more types of absorbent selected from a group comprised of activated carbon, activated carbon fiber, activated clay, acid clay, bentonite, diatom earth, silica gel, activated alumina and molecular sieve is employed as a solid absorbent for absorbing impurities contained in the light solution. Among those absorbents, clay, particularly acid clay treated with sulfuric acid is a preferable absorbent which is superior in the aspects of dealkaline effect, decoloring effect and deodorant effect. There is no particular requirement in grain size of the granulated absorbent, but in view of reducing the treatment time as short as possible and separating efficiently the absorbent from the light solution after the purification treatment, grain size of the absorbent is preferably in the range of 0.01 mm to 5 mm and, more preferably, in the range of 0.1 mm to 1.5 mm. When the grain size of the absorbent is smaller, effect of purification is superior, but separation after the purification treatment becomes more difficult. On the other hand, when the grain size of the absorbent is larger, separation after the treatment becomes easier, but effect of purification is inferior.

In the stirring and purifying tank 84, amount of addition of absorbent to the light solution is different depending on conditions of purification such as type of absorbent, grain size, stirring speed, temperature, etc. In case of employing an activated clay of 1 mm in average grain size, however, on conditions of room temperature, 300 rpm in stirring speed and 10 min in stirring time, a sufficient amount of addition of the activated clay is 0.5% by weight to 2.0% by weight.

The mixture of the light solution and absorbent after the purification is naturally separated just by leaving it stationary due to layer separation according to the difference in specific gravity between the light solution and absorbent. However, such a natural layer separation takes a long time until complete separation and is low in productivity. Therefore, in the apparatus according to the invention, the complete separation of the light solution and the absorbent from each other can be efficiently carried out by the solid-liquid centrifugal separator 88. The light solution flowing out of the solid-liquid centrifugal separator 88 is introduced in the purified light solution storage tank 92 to be stored therein as a final product, i.e., vegetable diesel fuel oil, and the absorbent is either wasted or recycled.

In the neutralization of the heavy solution of which principal component is glycerol, either phosphoric acid or sulfuric acid is employed as acid. Carbon dioxide can be used as a neutralizer, other than phosphoric acid and sulfuric acid. As carbon dioxide is transformed into potassium carbonate through reaction with a catalyst composed of alkaline material such as potassium hydroxide under the presence of water, same action as acid material of phosphoric acid and sulfuric acid is performed. When melting point or boiling point of salt contained in the neutralized heavy solution is higher, the neutralized heavy solution is more suitable for fuel of boiler, etc. For example, when neutralizing a heavy solution containing potassium hydroxide with phosphoric acid, the phosphoric acid and potassium hydroxide reacts on each other, and potassium phosphate is obtained. As the melting point of potassium phosphate is 1340° C. potassium phosphate is not dissolved in a furnace in which burning temperature of heavy solution is 800° C. to 1000° C. but remains in the form of ash content. Accordingly, there is no more such problem as corrosion of furnace wall or as environmental pollution due to poisonous gas produced by decomposition of salt. In addition, potassium phosphate which is the ash content may be not only industrially used as exchanging water material, desulfurizing agent of petroleum products, inflating agent, etc. but also used as an important agricultural fertilizer.

EXAMPLES

A production method of diesel fuel oil from a waste edible oil according to the present invention is hereinafter specifically described.

Example 1

In a production apparatus arranged as shown in FIGS. 1 to 5 and being capable of processing 5 tons/day, two sheets of superposed wire gauge of stainless steel of which number of mesh is 120 was used as the filter 12 mounted on the waste edible oil introduction chute 10 of the waste edible oil storage tank 14. Further, a polyester filament of which number of mesh is 300 was used as the cartridge filter 18 mounted on the strainer 16 installed on the outlet side of the waste edible oil storage tank 14. A waste edible oil (3.4 in acid value, 185 in saponification value, 112 in iodine value, 220° C. in flash point, 0.9% in moisture, and 1.3% in ash content)) is introduced from the waste edible oil introduction shoot 10 into the waste edible oil storage tank 14, and after natural sedimentation all the night through, a supernatant thereof was used. Potassium hydroxide (85% in purity) was used as a catalyst, and after dissolving the catalyst in methyl alcohol in the dissolving and stirring tank 50 at a rate of 100 parts by weight of methyl alcohol (99.8% in purity) to 11.5 parts by weight of the catalyst, a solution obtained thereby was moved to the catalyst containing alcohol solution tank 54. In addition, an activated clay (1 mm in average grain size) was used in the purification of the light solution, and phosphoric acid (85% in purity) was used in the neutralization of the heavy solution.

The steps of removal of the solid materials contained in the waste edible oil, heating, vacuum-dehydration and deodorization of the waste edible oil from which solid materials have been removed, reaction between the waste edible oil which has been vacuum-dehydrated and deodorized and the catalyst containing methyl alcohol solution, liquid-liquid separation of the reaction product, and solid-liquid separation of the purified light solution and the activated clay, were respectively carried out on the following operating conditions:

Mass flow rate of the waste edible oil measuring pump 22: 842 kg/h.

Mass flow rate of the catalyst containing alcohol solution measuring pump: 122 kg/h.

Temperature of the outlet of the shell and tube heat exchanger 24: 84° C.

Absolute pressure in the vacuum dehydrating and deodorizing tower 26: 60 mmHg.

Temperature of the inlet of the first stirring and reaction tank 60: 61° C.

Stirring speed of the stirring and reaction tanks 60: 350 rpm.

Centrifugal effect of the liquid-liquid centrifugal separator 68: 1,000 G.

Centrifugal effect of the solid-liquid centrifugal separator 88: 1,000 G.

The purification of the light solution separated by the liquid-liquid centrifugal separator 68 using the activated clay was carried out in the following semi-continuous operation:

Ratio by weight of the activated clay to the light solution: 1%.

Stirring speed of the stirring and purifying tank 84: 300 rpm.

Stirring time of the stirring and purifying tank 84: 10 min.

The purification of the heavy solution separated by the liquid-liquid centrifugal separator 68 using the phosphoric acid was carried out in the following operating condition of batch system:

Ratio by weight of the phosphoric acid to the heavy solution: 5.5%.

Stirring speed of the neutralizing and stirring tank 100: 100 rpm. stirring time of the neutralizing and stirring tank 100: 5 min.

On the mentioned conditions, the continuous process of removal of the solid materials contained in the waste edible oil, heating, vacuum-dehydration and deodorization of the waste edible oil from which solid materials have been removed, a reaction between the waste edible oil which has been vacuum-dehydrated and deodorized and the catalyst containing methyl alcohol solution, liquid-liquid separation of the reaction product, and solid-liquid separation of the purified light solution and the activated clay, semi-continuous process of removal of the light solution utilizing the activated clay, and batch process of the neutralization of the heavy solution utilizing the phosphoric acid were respectively carried out. The light solution and the neutralized heavy solution obtained in this manner were respectively kept stationary for 30 minutes in the purified light solution storage tank 92 and the heavy solution storage tank 106. Then, the purified light solution and the neutralized heavy solution were respectively sampled, and their characteristics were analyzed.

Concentration of odor material in the light solution was obtained in the following manner. That is, using a gas chromatograph (GC-14A, capillary column TC-1, 0.25 mmID, 15 mL), analysis was carried out under the conditions of 280° C. in inlet temperature, 250° C. in detector temperature, 40° C. for 5 min and 320° C. for 15 min in column temperature, 10° C./min in temperature rising speed, and 10μ—in sample injection amount. In the obtained chart, light component of which stay time is not longer than 20 min (except methyl alcohol) was considered an odor material, and concentration of the odor material was obtained from area of peak and considered a concentration of the odor material. Analysis of the other characteristics was carried out by the method prescribed in JIS standard on petroleum fraction or by normal method. Table 1 shows results of analysis of the characteristics of the purified light solution, and Table 2 shows results of analysis of the characteristics of the neutralized heavy solution, respectively. In Table 1, conversion of waste edible oil (%) means a yield of the light solution with respect to the waste edible oil, and is defined by the expression of [conversion of waste edible oil=amount of fatty acid alkyl ester/(amount of raw material waste edible oil—amount of impurities)×100%].

TABLE 1

|  | Example 1 | Example 2 | Comparative example 1 | Comparative example 2 | Comparative example 3 |
|---|---|---|---|---|---|
| Conversion of waste edible oil (%) | 99.5 | 99.8 | 91.3 | 84.0 | 65.0 |
| Cetane index | 57 | 59 | 51 | 48 | 48 |
| 90% distillation temperature (°C.) | 340 | 352 | 348 | 365 | 384 |
| Flashpoint (°C.) | 148 | 153 | 166 | 184 | 186 |
| Pour point (°C.) | −7 | −6 | −3 | −2 | −1 |
| Carbon residue (%) | 0.06 | 0.07 | 0.10 | 0.15 | 0.25 |
| Kinetic viscosity (m$^2$/s) | 6.21 | 6.84 | 7.56 | 8.26 | 8.58 |
| Calorific value (cal/g) | 9.440 | 9.520 | 9.220 | 9.340 | 9.225 |
| Specific gravity (25° C.) | 0.875 | 0.879 | 0.882 | 0.885 | 0.887 |
| Moisture (%) | 0.05 | 0.05 | 0.35 | 0.07 | 0.05 |
| Ash content (%) | 0.0034 | 0.0035 | 0.0060 | 0.0040 | 0.0035 |

TABLE 1-continued

|  | Example 1 | Example 2 | Comparative example 1 | Comparative example 2 | Comparative example 3 |
|---|---|---|---|---|---|
| Concentration of alkali (%) | not detected | not detected | not detected | 0.05 | 0.02 |
| Concentration of odor material (%) | 0.009 | 0.009 | 0.015 | 0.016 | 0.010 |
| Concentration of alcohol (%) | 0.50 | 0.65 | 0.99 | 1.24 | 1.30 |

TABLE 2

|  | Example 1 | Example 2 | Comparative example 1 | Comparative example 2 | Comparative example 3 |
|---|---|---|---|---|---|
| Composition |  |  |  |  |  |
| Glycerol (wt %) | 57.07 | 56.86 | 52.90 | 54.96 | 53.39 |
| Inorganic salt (wt %) | 9.11 | 9.10 | 10.2 | 9.82 | 9.80 |
| Alcohol (wt %) | 1.00 | 1.20 | 1.50 | 2.30 | 3.85 |
| Water (wt %) | 2.32 | 2.30 | 4.87 | 2.40 | 2.43 |
| Other impurities (wt %) | 30.50 | 30.54 | 30.53 | 30.52 | 30.53 |
| Characteristics |  |  |  |  |  |
| Specific gravity (25° C., g/cm$^3$) | 1.12 | 1.10 | 1.15 | 1.10 | 1.09 |
| Viscosity (25° C., mPa.s) | 519.7 | 503.5 | 498.2 | 502.6 | 500.5 |
| Quantity of heat (kcal/kg) | 5922 | 5910 | 5890 | 5943 | 5965 |

Example 2

Using the same production apparatus and on the same conditions as the foregoing example 1, a purified light solution and a neutralized heavy solution were obtained from a waste edible oil. In this example 2, ethyl alcohol (99.5% in purity) was used as an alcohol instead of methyl alcohol used in example 1, and mass flow rate of the catalyst containing alcohol solution measuring pump 56 was changed to 170 kg/h. Analysis of characteristics of the obtained light solution and heavy solution was also carried out in the same manner as the foregoing example 1. For calculating the concentration of the odor material contained in the light solution, in the obtained GC chart, light component of which stay time is not longer than 20 min (except methyl alcohol) was considered an odor material. Tables 1 and 2 show results of the analysis of characteristics.

Comparative Example 1

Using the same production apparatus and on the same conditions as the foregoing example 1, a purified light solution and a neutralized heavy solution were obtained from a waste edible oil. In case of this comparative example 1, in the apparatus shown in FIGS. 1 to 5, the passage between the outlet of the shell and heat exchanger 24 and the outlet of the dehydrated and deodorized waste edible oil measuring pump 58 was connected through a by-pass pipe line, whereby the waste edible oil flowing out of the heat exchanger 24 did not pass through the vacuum dehydrating and deodorizing tower 26 but flew directly in the stirring and reaction tank 60. Temperature of the waste edible oil at the outlet of the heat exchanger 24 was established to 62° C. Analysis of characteristics of the obtained light solution and heavy solution was also carried out in the same manner as the foregoing example 1. Tables 1 and 2 show results of the analysis.

Comparative Example 2

Using the same production apparatus and on the same conditions as the foregoing example 1, a purified light solution and a neutralized heavy solution were obtained from a waste edible oil. In case of this comparative example 1, sodium hydroxide (96% in purity) was used as a catalyst instead of potassium hydroxide, and the catalyst was dissolved in methyl alcohol in the dissolving and stirring tank 50 at a rate of 100 parts by weight of methyl alcohol (99.8% in purity) to 11.5 parts by weight of the catalyst. Analysis of characteristics of the obtained light solution and heavy solution was also carried out in the same manner as the foregoing example 1. Tables 1 and 2 show results of the analysis.

Comparative Example 3

Using the same production apparatus and on the same conditions as the foregoing example 1, a purified light solution and a neutralized heavy solution were obtained from a waste edible oil. In case of this comparative example 3, in the apparatus shown in FIGS. 1 to 5, the catalyst feeder 38 was moved from the dissolving and stirring tank 50 to the stirring and reaction tank 60, thus arrangement of the apparatus was partially changed so that the catalyst may be directly charged in the stirring and reaction tank 60. The catalyst (potassium hydroxide) was stored in the catalyst introduction shoot 40 of the catalyst feeder 38, and a methyl alcohol (99.8% in purity) was stored in the catalyst containing alcohol solution tank 54. Thus, for the reaction between the waste edible oil and methyl alcohol, the catalyst was inputted by the catalyst feeder 38 into the stirring and reaction tank 60 from the upper part thereof, and methyl alcohol was introduced by the measuring pump 56 into the stirring and reaction tank 60 from the bottom part thereof without dissolving the catalyst preliminarily in methyl alcohol.

The steps of removal of the solid materials contained in the waste edible oil, heating, vacuum-dehydration and deodorization of the waste edible oil from which solid materials have been removed, reaction between the waste edible oil which has been vacuum-dehydrated and deodorized and methyl alcohol, liquid-liquid separation of the reaction product, and solid-liquid separation of the purified light solution and the activated clay, were respectively carried out on the following operating conditions:

Mass flow rate of the waste edible oil measuring pump 22: 842 kg/h.

Mass flow rate of the measuring pump 56: 109 kg/h.

Supply speed of the catalyst from the catalyst feeder 38: 12.6 kg/h.

Temperature of the outlet of the shell and tube heat exchanger 24: 80° C.

Absolute pressure in the vacuum dehydrating and deodorizing tower 26: 55 mmHg.

Temperature of the inlet of the first stirring and reaction tank 60: 57° C.

Stirring speed of the stirring and reaction tanks 60: 350 rpm.

Centrifugal effect of the liquid-liquid centrifugal separator 68: 1,000 G.

Centrifugal effect of the solid-liquid centrifugal separator 88: 1,000G.

Analysis of characteristics of the obtained light solution and heavy solution was also carried out in the same manner as the foregoing example 1. Tables 1 and 2 show results of the analysis.

In summary, the invention defined in claim 1 is characterized by obtaining a diesel fuel oil from a waste edible oil through the steps of: removing solid materials contained in a waste edible oil dumped from restaurant, food plant, home, etc. therefrom; heating said waste edible oil from which solid materials have been removed to a predetermined temperature, thereby removing moisture and materials of odor contained in the waste edible oil therefrom by evaporation; dissolving in alcohol a catalyst containing at least one type or more types of alkaline material selected from a group comprised of at least potassium hydroxide, potassium carbonate and potassium alcoholate, thereby preparing an alcoholic solution containing the catalyst; mixing said waste edible oil from which said solid materials, moisture and materials of odor have been removed with said alcoholic solution containing the catalyst and stirring the waste edible oil and alcoholic solution, thereby accelerating a catalytic reaction between the waste edible oil and the alcohol and obtaining a reaction product between the waste edible oil and the alcohol; separating said reaction product into a light solution and a heavy solution; mixing the light solution obtained in the separation step with a solid absorbent, thereby impurities such as residual catalyst, odor material, moisture contained in the light solution being absorbed by the solid absorbent; and separating and removing said solid absorbent from a mixture of the solid absorbent having absorbed the impurities and the light solution.

The invention defined in claim 2 is characterized in that the production method as defined in claim 1 further comprises the step of mixing the heavy solution obtained in the step of separating the reaction product into the light solution and the heavy solution with a neutralizer to neutralize the catalyst composed of alkaline material contained in the heavy solution.

In the production method defined in claim 2, it is possible to recycle the heavy solution separated from the reaction product to be a fuel or a raw material for producing glycerol for industrial use. That is, as the heavy solution separated from the reaction product includes most part of the catalyst used in the reaction other than the glycerol which is a principal component, when using the heavy solution as it is as a fuel or as a raw material of glycerol for industrial use, the apparatus may be corroded by alkali. In the production method as defined in claim 2, however, since the heavy solution is mixed with a neutralizer so that the catalyst composed of any alkaline material contained in the heavy solution may be neutralized, it becomes possible to recycle the glycerol which is a by-product of the ester exchange reaction between the waste edible oil and alcohol to be used as a fuel for boiler, thermal recovery incinerator, etc. or as a raw material of producing glycerol for industrial use, as it is.

The invention defined in claim 3 is characterized in that, a diesel fuel oil is obtained by carrying out semi-continuously each step of the production method as defined in claim 1 or 2.

The invention defined in claim 4 is characterized in that, in the production method as defined in claim 1 or 2, the heated waste edible oil is left under a vacuum pressure reduction in the step of removing the moisture and odor material from the waste edible oil. In this production method, since heated waste edible oil is left under a vacuum pressure reduction, the moisture and odor material are speedily evaporated from the waste edible oil, thus the removal of the moisture and odor material from the waste edible oil being carried out in a short time with a high efficiency.

The invention defined in claim 5 is characterized in that, in the production method as defined in claim 1 or 2, the steps of separating the reaction product into the light solution and the heavy solution and separating the solid absorbent from the mixture of the solid absorbent having absorbed impurities and the light solution are respectively carried out by centrifugation. In this production method, as compared with the stationary layer separation utilizing a difference in specific gravity, the separation of the reaction product into the light solution principally composed of fatty acid alkyl ester and the heavy solution principally composed of glycerol and the separation of the solid absorbent from the mixture of the solid absorbent having absorbed impurities and the light solution are respectively carried out in a short time with a high efficiency.

The invention defined in claim 6 is characterized in that, in the production method as defined in claim 1 or 2, the solid material, moisture and odor material contained in the waste edible oil dumped from restaurant, food plant, home, etc. are removed so that content of the solid material is 0.05% or less, content of the moisture is 0.03% or less, and content of the odor material is 10 ppm or less, respectively. In this production method, the solid material, moisture and odor material contained in the waste edible oil are removed with a high efficiency, thus the mentioned function of the invention defined in claim 1 may be exactly performed.

The invention defined in claim 7 is characterized in that, in the production method as defined in claim 1 or 2, the alcohol is one type or more types of alcohol selected from a group comprised of alkyl alcohol of which number of carbon is 1 to 10 such as methyl alcohol, ethyl alcohol, isobutyl alcohol, and amount of addition of alcohol to the waste edible oil is equal to a stoichiometric quantity with respect to amount of glyceride in the waste edible oil or larger than the stoichiometric quantity by 10%. In this production method, almost all quantity of the glyceride in the waste edible oil is converted to a fatty acid alkyl ester by the ester exchange reaction with alcohol as shown in the foregoing chemical formula.

The invention defined in claim 8 is characterized in that, in the production method as defined in claim 1 or 2, amount of addition of catalyst to alcohol is in the range of 0.3% by weight to 3.0% by weight. In this production method, conversion rate of the waste edible oil to fatty acid alkyl ester is kept high, and there is no possibility that the side reaction of producing fatty acid soap takes place easily due to excessive amount of addition of catalyst. There is no possibility of strong corrosion on the reactor due to excessive amount of addition of catalyst, either.

The invention defined in claim 9 is characterized in that, in the production method as defined in claim 1 or 2, the reaction between the waste edible oil and alcohol is performed in the temperature range of 25° C. to 240° C. and in the pressure range of atmospheric pressure to 78.5 kg/cm$^2$. As a result, conversion rate of the waste edible oil to the fatty acid alkyl ester is kept high.

The invention defined in claim 10 is characterized in that, in the production method as defined in claim 1 or 2, phosphoric acid, sulfuric acid or carbon dioxide is employed as the neutralizer for neutralizing the catalyst composed of alkaline material contained in the heavy solution. In this production method, as a result of neutralizing reaction between the catalyst composed of alkaline material contained in the heavy solution and the phosphoric acid or sulfuric acid, a neutral heavy solution is obtained. The carbon dioxide becomes a potassium carbonate ($K_2CO_3$) by reaction with the catalyst composed of alkaline material such as potassium hydroxide under the existence of water, and performs the same function as the acidic material such as phosphoric acid or sulfuric acid.

The invention defined in claim 11 is characterized in that, in the production method as defined in claim 1 or 2, one type of absorbent or a mixture of two or more types of absorbent selected from a group comprised of activated carbon, activated carbon fiber, activated clay, acid clay, bentonite, diatom earth, silica gel, activated alumina and molecular sieve is employed as a solid absorbent for absorbing impurities contained in the light solution. In this production method, the impurities contained in the light solution are absorbed by the solid absorbent with high efficiency. In particular, the acid clay is a preferable absorbent which is excellent in the aspects of dealkaline effect, decoloring effect and deodorant effect.

The invention defined in claim 12 is a production apparatus for producing a diesel fuel oil from a waste edible oil comprising: a waste edible oil storage tank for storing a waste edible oil dumped from restaurant, food plant, home, etc.; solid material removing means for removing solid materials contained in said waste edible oil therefrom; waste edible oil heating means for heating said waste edible oil from which solid materials have been removed to a predetermined temperature; dehydrating and deodorizing means for removing moisture and odor material contained in said heated waste edible oil by evaporation therefrom; a dissolving and stirring tank for mixing a catalyst composed of an alkaline material with alcohol and stirring the catalyst and alkaline material, thereby preparing a catalyst containing alcohol solution in which the catalyst is dissolved; alcohol supplying means for supplying an alcohol to said dissolving and stirring tank; catalyst supplying means for supplying the catalyst to said dissolving and stirring tank; a stirring and reaction tank for mixing said waster edible oil from which solid materials moisture and odor material have been removed with said alcohol solution containing the catalyst, and accelerating a catalytic reaction between the waste edible oil and alcohol, thereby obtaining a reaction product between the waste edible oil and alcohol; liquid-liquid separating means for separating said reaction product into a light solution and a heavy solution; a stirring and purifying tank for mixing and stirring said light solution obtained by separation from said reaction product with a solid absorbent so that impurities contained in the light solution such as residual oxygen, odor material, coloring material, moisture, etc. are absorbed by the solid absorbent; absorbent supplying means for supplying the solid absorbent to said stirring and purifying tank; and solid-liquid separating means for separating and removing the solid absorbent from a mixture of said solid absorbent having absorbed the impurities and said light solution.

The invention defined in claim 13 is characterized in that the production apparatus as defined in claim 12 further comprises a neutralizing and stirring tank for mixing and stirring the heavy solution obtained by the separation from the reaction product with a neutralizer so that the catalyst composed of an alkaline material contained in the heavy solution is neutralized, and neutralizer supplying means for supplying a neutralizer to said neutralizing and stirring tank.

In the production apparatus according to the invention defined in claim 13, since the heavy solution is mixed with the neutralizer in the neutralizing and stirring tank so that the catalyst composed of an alkaline material contained in the heavy solution is neutralized, it becomes possible to recycle glycerol, which is a by-product of the ester exchange reaction between the waste edible oil and alcohol, as a fuel for boiler, heat recovery type incinerator, etc. or as a raw material of glycerol for industrial use as it is, without dumping it to be an environmental pollution material.

The invention defined in claim 14 is characterized in that, in the production apparatus as defined in claim 12 or 13, the mentioned dehydrating and deodorizing means is provided with vacuum suction means for putting the heated waste edible oil under a vacuum pressure reduction. In this production apparatus, as moisture and odor material evaporate speedily from the waste edible oil as a result of putting the heated waste edible oil under a vacuum pressure reduction by the vacuum suction means, removal of the moisture and odor material from the waste edible oil can be carried out in a short time with a high efficiency by the dehydrating and deodorizing means.

The invention defined in claim 15 is characterized in that, in the production apparatus as defined in claim 12 or 13, centrifugal separators are respectively employed as the mentioned liquid-liquid separating means and the solid-liquid separating means. In this production apparatus, as the separation of the light solution principally composed of fatty acid alkyl ester from the heavy solution principally composed of glycerol and the separation of the solid absorbent from the mixture of the solid absorbent having absorbed the impurities and the light solution are respectively carried out by the centrifugal separators, the respective operations of separation can be performed in a short time with a high efficiency as compared with the stationary layer separation utilizing a difference in specific gravity.

In effect, in the production method of a diesel fuel oil according to the invention as defined in claim 1, by utilizing the waste edible oil dumped from restaurant, food industries, home, etc. and substantially not recycled as a raw material, it becomes possible to obtain a vegetable diesel fuel oil of enough quality to be satisfied as a fuel oil for diesel engine vehicles such as motor truck, garbage wagon, bus, etc., and of which contents of sulfide and nitride are considerably low as compared with the conventional diesel fuel oil derived from petroleum. As a result, the invention contributes significantly to the promotion of effective utilization of food resources and to the protection of environment of the earth. Further, in the production method according to the invention as defined in claim 2, since glycerol which is a by-product of the ester exchange reaction between the waste edible oil and alcohol can be recycled to be used as a fuel for boilers, heat recovery type incinerator, etc., or as a raw material of glycerol for industrial use in addition to the above advantages, the invention contributes to the protection of environment of earth all the more.

In the production apparatus of a diesel fuel oil according to the invention as defined in claim 12, by utilizing the waste edible oil dumped from restaurant, food industries, home, etc. and substantially not recycled as a raw material, it becomes possible to obtain a vegetable diesel fuel oil of enough quality as mentioned above, which contributes to the promotion of effective utilization of food resources and to the protection of environment of the earth. Further, in the production apparatus according to the invention as defined in claim 13, glycerol which is a by-product of the ester exchange reaction between the waste edible oil and alcohol can be recycled to be used as a fuel for boilers, heat recovery type incinerator, etc., or as a raw material of glycerol for industrial use.

It should also be understood that the foregoing relates to only a preferred embodiment of the invention, and that it is intended to cover all changes and modifications of the example of the invention herein chosen for the purposes of the disclosure, which do not constitute departures form the spirit and scope of the invention.

What is claimed is:

1. A production method of a diesel fuel from a waste edible oil through the steps of:

removing solid materials contained in a waste edible oil therefrom;

heating said waste edible oil from which solid materials have been removed to 25–200° C., thereby removing moisture and materials of odor contained in the waste edible oil therefrom by evaporation;

dissolving in alcohol a catalyst containing at least one or more alkaline material selected from the group consisting of potassium hydroxide, potassium carbonate and potassium alcoholate and mixtures thereof, thereby preparing an alcoholic solution containing the catalyst;

mixing said waste edible oil from which said solid materials, moisture and materials of odor have been removed with said alcoholic solution containing the catalyst and stirring the waste edible oil and alcoholic solution, thereby accelerating a catalytic reaction between the waste edible oil and the alcohol and obtaining a reaction product between the waste edible oil and the alcohol;

separating said reaction product into a light solution and a heavy solution;

mixing the light solution obtained in said separation step with a solid absorbent, thereby impurities contained in the light solution being absorbed by the solid absorbent; and separating and removing said solid absorbent from a mixture of the solid absorbent having absorbed the impurities and the light solution.

2. A production method as defined in claim 1, further comprising the step of mixing the heavy solution obtained in said step of separating the reaction product into the light solution and the heavy solution with a neutralizer to neutralize the catalyst composed of alkaline material contained in the heavy solution.

3. A production method as defined in claim 1 or 2, wherein each step of a series of said production method is carried out semi-continuously.

4. A production method as defined in claim 1 or 2, wherein the heated waste edible oil is left under a vacuum pressure reduction in the step of removing the moisture and odor material from the waste edible oil.

5. A production method as defined in claim 1 or 2, wherein the steps of separating the reaction product into the light solution and the heavy solution and separating the solid absorbent from the mixture of the solid absorbent having absorbed impurities and the light solution are respectively carried out by centrifugation.

6. A production method as defined in claim 1 or 2, wherein the solid material, moisture and odor material contained in the waste edible oil are removed so that the content of solid material is 0.05% or less, the moisture content is 0.03% or less, and the content of the odor material is 10 ppm or less, respectively.

7. A production method as defined in claim 1 or 2, wherein the alcohol is one or more alcohol selected from the group consisting of alkyl alcohols containing 1 to 10 carbon atoms, wherein the amount of alcohol added to the waste edible oil is equal to a stoichiometric quantity with respect to amount of glyceride in the waste edible oil or larger than stoichiometric quantity by 10%.

8. The production method as defined in claim 7, wherein the alcohol is selected from the group consisting of methyl alcohol, ethyl alcohol, isobutyl alcohol and mixtures thereof.

9. A production method as defined in claim 1 or 2, wherein amount of addition of catalyst to alcohol is in the range of 0.3% by weight to 3.0% by weight.

10. A production method as defined in claim 1 or 2, wherein the reaction between the waste edible oil and alcohol is performed in the temperature range of 25° C. to 240° C. and in the pressure range of atmospheric pressure to 78.5 kg/cm$^2$.

11. A production method as defined in claim 2, wherein phosphoric acid, sulfuric acid or carbon dioxide is employed as the neutralizer for neutralizing the catalyst composed of alkaline material contained in the heavy solution.

12. A production method as defined in claim 1 or 2, wherein the absorbent is one or more absorbent selected from the group consisting of activated carbon, activated carbon fiber, activated clay, acid clay, bentonite, diatom earth, silica gel, activated alumina and molecular sieve.

13. The production method as defined in claim 1, wherein said impurities are selected from the group consisting of residual catalyst, odor material, moisture, and mixtures thereof.

\* \* \* \* \*